(12) United States Patent
Knerr et al.

(10) Patent No.: US 6,673,376 B1
(45) Date of Patent: Jan. 6, 2004

(54) METHOD OF PREPARING A SOLUTION, IN PARTICULAR A DIALYSIS OR INFUSION SOLUTION

(75) Inventors: Thomas Knerr, St. Wendel (DE); Wendelin Backhaus, Weilmünster (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 09/434,847

(22) Filed: Nov. 4, 1999

(30) Foreign Application Priority Data

Nov. 4, 1998 (DE) ......................... 198 50 830

(51) Int. Cl.[7] .................... A61K 33/00; A61K 31/185; A61K 33/14
(52) U.S. Cl. ................ 424/717; 424/680; 514/553; 514/557; 514/561; 514/574
(58) Field of Search ................ 424/44, 717, 680; 514/557, 561, 574, 553

(56) References Cited

U.S. PATENT DOCUMENTS

| | | | |
|---|---|---|---|
| 4,489,535 A | * 12/1984 | Veltman | 53/431 |
| 5,211,643 A | * 5/1993 | Reinhardt et al. | 604/416 |
| 5,385,564 A | * 1/1995 | Slater et al. | 604/416 |
| 5,645,734 A | * 7/1997 | Kenley et al. | 210/805 |
| 5,827,820 A | * 10/1998 | duMoulin et al. | 514/2 |
| 5,871,477 A | * 2/1999 | Isono et al. | 604/410 |

FOREIGN PATENT DOCUMENTS

| | | |
|---|---|---|
| DE | 39 17 251 | 11/1990 |
| DE | 41 25 819 | 2/1993 |
| DE | 90 07 814 | 2/1997 |
| EP | 0 526 754 | 2/1993 |
| EP | 0 456 806 B1 | * 12/1996 |
| JP | 4-257522 | * 9/1992 |
| JP | 10-87478 | * 4/1998 |

OTHER PUBLICATIONS

Remington's Pharmaceutical Sciences (17th Ed., 1985), pp. 243–245.*

* cited by examiner

Primary Examiner—Thurman K. Page
Assistant Examiner—Frank Choi
(74) Attorney, Agent, or Firm—Kenyon & Kenyon

(57) ABSTRACT

A method of preparing a solution is described, in particular a dialysis or infusion solution, and a storage system for preparing such a solution. An acid-reacting component comprising a solid acid and/or a solid salt which is water-soluble and is not hygroscopic, is dissolved in water in a first container and mixed with an alkaline-reacting bicarbonate solution in a second container. The quantity ratios are selected so that the acid and/or salt content does not exceed 6 mmol per liter of finished solution and the bicarbonate content does not exceed 40 mmol per liter of finished solution.

19 Claims, 1 Drawing Sheet

METHOD OF PREPARING A SOLUTION, IN PARTICULAR A DIALYSIS OR INFUSION SOLUTION

The present invention relates to a method of preparing a solution, in particular a dialysis or infusion solution. This invention also concerns a solution, in particular a dialysis or infusion solution, as well as a storage system for preparing such a solution.

DESCRIPTION OF RELATED ART

Dialysis solutions that have as close to a physiological pH as possible must be prepared for use in hemodialysis as well as in peritoneal dialysis. These solutions having a pH of approximately 7.4, and containing important electrolytes, also contain a physiological buffer system suitable for establishing the desired pH. Since bicarbonate is the physiological buffer found in blood, bicarbonate is generally used as the buffer system for these solutions.

An important disadvantage of a bicarbonate buffer system is that it releases $CO_2$ at a low pH due to outgassing, and is thus unstable. In practice the pH must be kept relatively high to prevent the release of gas. In the presence of appropriate cations, however, the cations can be precipitated with the carbonate at a high pH. This is true, for example, of calcium and magnesium ions usually present in dialysis solutions.

To establish the desired physiological pH of the dialysis solution, a second buffer system is used for buffering, usually containing acetate or other metabolizable acids. To prevent outgassing of a solution containing bicarbonate, while also preventing precipitation of carbonates which occurs especially at high pH, dialysis solutions are usually prepared from two individual solutions stored separately. A first solution containing bicarbonate is stored in one tank, and a second solution, an acidic buffer system, is stored in another tank. The acid component usually also contains the electrolytes needed for dialysis, such as NaCl or KCl.

To prepare a ready-to-use solution, the aforementioned individual solutions are mixed, with the risk of precipitation of carbonate being of only minor importance because the dwell time of the finished dialysis solution in the pipeline system of the dialysis machine is only on the order of approximately one minute.

The solution containing the acid component as well as the solution containing the bicarbonate are usually supplied in the form of concentrate canisters, which are mixed on site and diluted with ultrahigh purity water to the desired concentration. The concentrate is prepared in conventional commercial tanks with a capacity of approximately 10 l. This practice not only leads to considerable difficulties in handling the tanks, but also incurs a considerable expense for storage of the concentrates because different concentrates must be used.

European Patent 526,754 describes the preparation of such a dialysis solution by mixing two individual solutions, where one of the individual solutions is an alkaline reacting bicarbonate solution and the other is a bicarbonate-free acid solution. The acid solution contains metabolizable organic acids, while the essential ingredients of the individual alkaline solution are alkali carbonate and alkali bicarbonate.

To avoid the problem of complicated handling of the concentrate tanks, proposals exist for supplying the substances needed for dialysis in the form of solids, and preparing the required concentrates by dissolving the solids on site. However, with this method it is difficult to use solid acids, which are generally too hygroscopic or unsuitable for adjusting to an optimum pH, especially at a high bicarbonate concentration.

SUMMARY OF THE INVENTION

The present invention relates to a solution, in particular an infusion solution or a dialysis solution, that requires only little preparation work and is physiologically tolerable.

In one aspect, the present invention is a method of preparing a dialysis or infusion solution, comprising the steps of dissolving in water in a first container an acid-reacting component that includes at least one of a solid acid and a solid salt, said acid-reacting component being water-soluble and not hygroscopic, and mixing said dissolved acid-reacting component with an alkaline reacting bicarbonate solution in a second container. The method further includes selecting quantity ratios of acid-reacting component and bicarbonate so that an acid-reacting component content does not exceed about 6 mmol per liter of solution, and a bicarbonate content does not exceed about 40 mmol per liter of solution.

In a different aspect, the invention is a dialysis or infusion solution, comprising an alkaline-reacting bicarbonate component and an acid-reacting component comprising at least one of an acid and a salt. The at least one of an acid and a salt are water-soluble and not hygroscopic solids, and the acid and salt content does not exceed about 6 mmol per liter of finished solution, while the alkaline-reacting bicarbonate content does not exceed about 40 mmol per liter of finished solution.

In a third aspect, the invention is a storage system for preparing a dialysis or infusion solution, that includes a first container adapted for containing an acid-reacting component and a second container adapted for containing an alkaline-reacting bicarbonate component. The acid-reacting component is formed of at least one of a solid acid and a solid salt which is water-soluble and not hygroscopic. This has a buffer capacity resulting in a finished solution having an acid and salt concentration of no greater than about 6 mmol per liter of solution and a bicarbonate concentration of up to about 40 mmol per liter of solution.

According to this invention, the method for preparing a solution, in particular a dialysis or infusion solution, includes dissolving in water a component that yields an acid, including a solid acid and/or a solid salt which is water-soluble and not hygroscopic. This step preferably occurs in a first container. The solution can then be mixed with an alkaline reacting bicarbonate solution in a second container, with the quantity ratios being selected so that the acid and/or salt content does not exceed, for example, 6 mmol per liter of finished solution, and the bicarbonate content does not exceed, for example, 40 mmol per liter.

Because of the solid nature of the acid or salt used, preparing such a solution is not problematical. After dissolving the acid or salt in the first container, this solution is mixed with the bicarbonate solution, and despite a relatively high bicarbonate content preferably of up to 40 mmol per liter of finished solution, an acid and/or salt content of less than about 6 mmol per liter of finished solution is sufficient to prepare a physiologically tolerable solution.

In another embodiment of the present invention, the mixture of the solution containing the acid-reacting component and the alkaline reacting bicarbonate solution is diluted with water before being used. Accordingly, a concentrate is first formed from the acid or salt present in the form of a solid in the container, and the concentrate is then diluted with water to the desired value, before or after being mixed with the alkaline reacting bicarbonate solution.

In yet another embodiment of the present invention, the bicarbonate is used in the form of a solid, and the alkaline reacting bicarbonate solution is prepared by dissolving the solid. Such a procedure has the advantage that the use of solids as starting materials simplifies both the preparation and storage of the materials. Thus, according to this invention, the alkaline reacting bicarbonate solution can be prepared in the second container using a solid containing bicarbonate.

It is especially advantageous if the carbonate content per liter of finished solution is in the range between 32 and 35 mmol, to compensate for metabolic acidosis of patients with renal failure.

According to a preferred embodiment of the present invention, the acid and/or salt content per liter of finished solution is $\leq 6$ meq, and more preferably 2–4 meq. Despite relatively high bicarbonate concentrations of up to 40 mmol/l, an acid and/or salt content of less than 6 meq per liter of finished solution, preferably of 2–4 meq/l, is sufficient to buffer the finished solution to the physiological pH of approximately 7.4.

A further embodiment of the present invention provides for the use of citric acid, isocitric acid, 2-oxoglutaric acid, succinic acid, fumaric acid, malic acid and/or oxalic acid and the salts thereof as respectively the acid and the salt forming the solution. In addition, hydrochlorides of amino acids and the salts thereof may also be used in the same manner.

The present invention also relates to a dialysis or infusion solution having a bicarbonate component that can be used to produce an alkaline reaction, and an acid-reacting component which includes an acid and/or a salt. The acid and the salt are present in the form of solids under normal conditions. For example, the salt and/or acid content preferably does not exceed 6 mmol per liter of finished solution, and the bicarbonate content preferably does not exceed 40 mmol/l.

It is especially advantageous if the bicarbonate content per liter of finished solution is in the range of between 32 and 35 mmol per liter of finished solution. The acid and/or salt content per liter of finished solution may be $\leq 6$ meq/l, and preferably 2–4 meq/l.

As described above, it is also especially advantageous if the acid or salt used in the solution is citric acid, isocitric acid, 2-oxoglutaric acid, succinic acid, fumaric acid, malic acid and/or oxalic acid and the salts thereof. Likewise, the hydrochlorides of amino acids and the salts thereof may also be used.

The present invention also relates to a system for preparing a solution, in particular a dialysis or infusion solution, that uses at least two storage tanks or containers. An acid-reacting component is stored in one of the containers, and an alkaline-reacting bicarbonate component is stored in the other container. The acid-reacting component includes a solid acid and/or a solid salt which is water-soluble and not hygroscopic. The components have a buffer capacity such that a physiological pH can be established in the finished solution at an acid and/or salt concentration of $\leq 6$ mmol per liter of finished solution and a bicarbonate concentration of up to 40 mmol per liter of finished solution.

Another embodiment of this invention provides for the alkaline-reacting bicarbonate component in the container to be present in the form of a solid.

According to another preferred embodiment of the present invention, three containers are provided, with the first container holding an acid-reacting component, the second container holding an alkaline-reacting bicarbonate component and the third container holding additives.

It is especially advantageous if all the components and additives in the containers are in the form of solids. The additives may include NaCl.

DETAILED DESCRIPTION OF THE INVENTION

Figure 1:
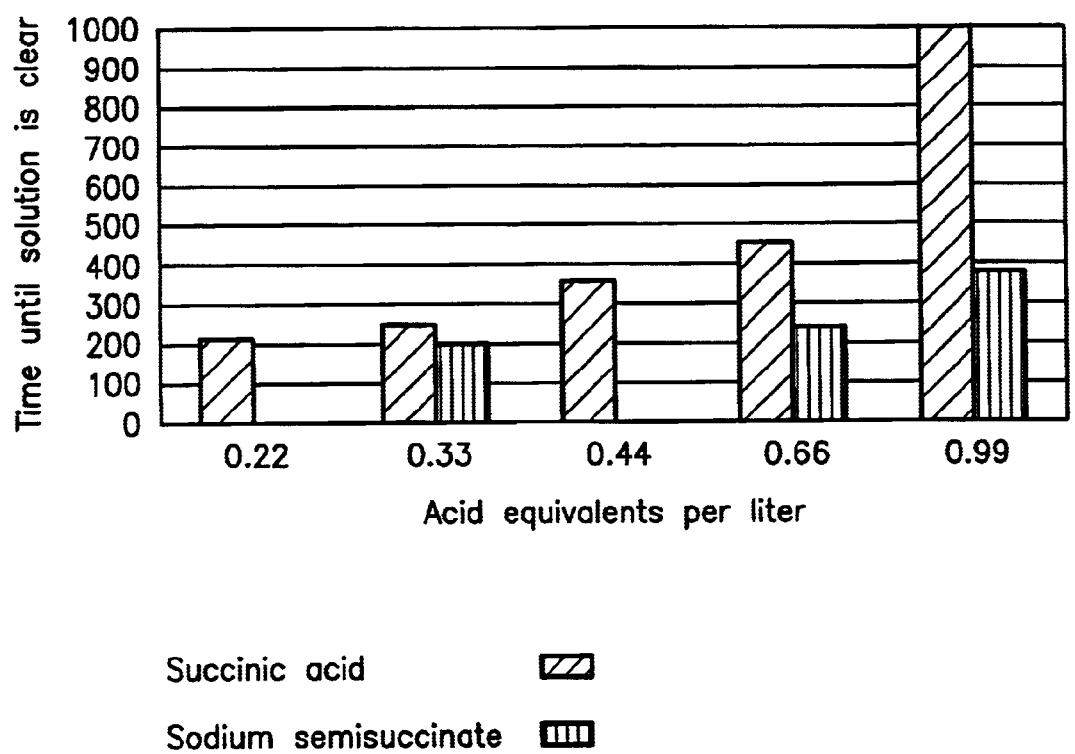
FIG. 1 is a plot showing the time required for a solution to become clear, plotted against acid equivalents per liter.

Additional details and advantages of the present invention are explained in greater detail on the basis of the following preferred embodiments.

The following table shows the pH values of a finished dialysis solution formed using succinic acid as the solid acid. Succinic acid was dissolved in water to prepare a 0.15 molar succinic acid solution. This concentrate was then mixed with a 1 molar sodium bi-carbonate solution and diluted with the stated amount of water.

| | Bicarbonate-succinate mixed pH values | | | | |
|---|---|---|---|---|---|
| NaHCO$_3$ | water | succinic | 1$^{st}$ test | 2$^{nd}$ test | 3$^{rd}$ test |
| 35 mL | 957 mL | 8 mL | 7.42 | 7.39 | 7.41 |
| 35 mL | 955 mL | 10 mL | 7.26 | 7.27 | 7.27 |
| 35 mL | 953 mL | 12 mL | 7.16 | 7.17 | 7.16 |
| 35 mL | 951 mL | 14 mL | 7.08 | 7.09 | 7.08 |
| 40 mL | 952 mL | 8 mL | 7.46 | 7.47 | 7.48 |
| 40 mL | 950 mL | 10 mL | 7.34 | 7.35 | 7.32 |
| 40 mL | 948 mL | 12 mL | 7.24 | 7.25 | 7.24 |
| 40 mL | 946 mL | 14 mL | 7.14 | 7.16 | 7.19 |

This table shows that succinic acid in a concentration of 1.5 mmol/L, for example, in terms of the finished ready-to-use solution, is sufficient to adjust a physiological pH despite the relatively high sodium bicarbonate concentration.

Use of succinic acid according to the present embodiment, or use of other acids and/or salts according to the present invention is not limited only to producing dialysis solutions for hemodialysis, but instead this method can also be used to prepare solutions for peritoneal dialysis.

The storage system required for preparing a solution according to this invention, in particular an infusion or dialysis solution, may also consist of three containers or storage tanks containing dry concentrates. For example, the first container may contain the acid-reacting component such as succinic acid, the second container may hold sodium hydrogen carbonate and the third container may contain sodium chloride. The first container may also contain a mixture of other ingredients, such as potassium chloride. Saturated solutions can be prepared from the sodium hydrogen carbonate and the sodium chloride at the dialysis machine, and then can be diluted to the ready-to-use solution in the further steps. The acid-reacting component such as succinic acid, however, should be dissolved in a fixed volume of water during a batch preparation, and then should be processed further to obtain a defined concentrate.

The rate at which the acid or the salt dissolves in water is an important consideration for this process. The concentrate may be, for example, an approximately 110-fold concentration, meaning that one liter of the concentrate of the acid-reacting component is mixed with approximately 109 liters of water or salt solution to prepare the ready-to-use solution. If succinic acid is used, preferably approximately 0.165 mol or 19.47 g succinic acid is dissolved in one liter of concentrate.

Although the solubility of succinic acid is adequate in principle, its dissolution rate is very low. Furthermore, because of the specific nature of the succinic acid crystals, flotation can occur with some of the material, which is thus removed from the mixing zone. The simultaneous presence of other salts and glucose can further lower the solubility and dissolution rate of succinic acid.

The dissolution rate of succinic acid can thus be advantageously increased by partial neutralization using a base. To do so, one equivalent of succinic acid is dissolved, optionally by heating, in the smallest possible volume of water and mixed with approximately 0.05 to 0.5, and preferably 0.25, equivalents of base. The completely dissolved product is subjected to a conventional drying operation such as, for example spray drying, freeze drying, etc. and then homogenized. Preferred bases include soda lye, sodium hydroxide, sodium carbonate and sodium bicarbonate, because the physiologically safe sodium salts of succinic acid are formed with these bases. The container holding the acid-reacting component may contain potassium, magnesium and calcium salts in suitable amounts, and the hydroxides, oxides, hydrogen carbonates and carbonates of these cations are also suitable bases.

The increase in dissolving rate is illustrated by the following example.

In a beaker, 0.2 mol succinic acid and 0.1 mol sodium hydrogen carbonate are mixed with 100 ml water. This solution is stirred and heated briefly until all the solids have dissolved. Then the solution is dried to constant weight (for approximately 48 hours) at approximately 105° C. in a drying oven. The product, which forms amorphous crystals, is homogenized in a mortar.

The following table shows the dissolution rate of succinic acid and the resulting succinic acid sodium hydrogen carbonate adduct.

Dissolving rate of succinic acid and succinic acid-$NaHC_3$

| Succinic acid | Concentrate | Time until solution is clear | | | Average |
|---|---|---|---|---|---|
| 12.98 g/L ≅ 0.11 mol/l | 0.22 meq/L | 200 | 210 | 220 | 210 |
| 19.47 g/L ≅ 0.165 mol/l | 0.33 meq/L | 230 | 250 | 270 | 250 |
| 25.96 g/L ≅ 0.22 mol/L | 0.44 meq/L | 400 | 375 | 300 | 358 |
| 38.94 g/L ≅ 0.33 mol/L | 0.66 meq/L | 510 | 420 | 450 | 460 |
| 58.11 g/L ≅ 0.495 mol/L adduct ≅ free succinic acid | 0.99 meq/L | 900 | >1080 | 960 | >900 |
| 28.38 g/L ≅ 0.11 mol/L | 0.33 meq/L | 200 | 210 | 170 | 193 |
| 56.76 g/L ≅ 0.22 mol/L | 0.66 meq/L | 260 | 230 | 240 | 243 |
| 85.14 g/L ≅ 0.33 mol/L | 0.99 meq/L | 390 | 400 | 360 | 383 |

The acceleration in dissolving rate is illustrated in the graph shown in FIG. 1, where the x axis has been scaled to show acid equivalents per liter of solution. In the relevant concentration range, the dissolving rate of the partial sodium salt is 20–40% greater than that of the pure acid.

It will be apparent to those skilled in the art that various modifications and variations can be made in the structure and methodology of the present invention, without departing from the spirit or scope of the invention. Thus, it is intended that the present invention covers the modifications and variations of this invention provided they come within the scope of the appended claims and their equivalents.

What is claimed is:

1. A method of preparing a dialysis or infusion solution, comprising the steps of:

dissolving in a first container an acid-reacting component comprising at least one of a solid acid and a solid salt, said acid-reacting component being water-soluble and non-hygroscopic;

selecting quantity ratios of the acid-reacting component and an alkaline-reacting bicarbonate solution so that an acid-reacting component content does not exceed about 6 mmol per liter of solution, and an alkaline-reacting bicarbonate content does not exceed about 40 mmol per liter of solution; and mixing said dissolved acid-reacting component with the alkaline reacting bicarbonate solution in a second container.

2. The method according to claim 1, further comprising the step of diluting with water the mixture of the solution containing the acid-reacting component and the alkaline-reacting bicarbonate solution.

3. The method according to claim 1, further comprising the step of preparing the alkaline-reacting bicarbonate solution by dissolving solid bicarbonate.

4. The method according to claim 1, further comprising the step of selecting the quantity ratios of acid-reacting component and alkaline-reacting bicarbonate to obtain the bicarbonate content of the finished solution in a range between about 32 and 35 mmol per liter.

5. The method according to claim 1, further comprising the step of selecting a content of the at least one of a solid acid and a solid salt to be no greater than approximately 6 meq per liter.

6. The method according to claim 5, further comprising the step of selecting a content of the at least one of a solid acid and a solid salt to be in the range of approximately 2 to 4 meq per liter of finished solution.

7. The method according to claim 1, further comprising the step of selecting as the solid acid and solid salt one of the group consisting of citric acid, isocitric acid, 2-oxoglutaric acid, succinic acid, fumaric acid, malic acid, oxalic acid and the salts thereof.

8. The method according to claim 1, further comprising the step of selecting as the solid acid and solid salt at least one of hydrochlorides of amino acids and the salts thereof.

9. A dialysis or infusion solution, comprising:

an alkaline-reacting bicarbonate component; and an acid-reacting component comprising at least one of an acid and a salt, wherein the acid-reacting component is a water-soluble and non hygroscopic solid, and wherein the acid-reacting component concentration is less than about 6 mmol per liter of finished solution, and an alkaline-reacting bicarbonate concentration is less than about 40 mmol per liter of finished solution.

10. The solution according to claim 9, wherein the alkaline-reacting bicarbonate concentration is in the range between approximately 32 and 35 mmol per liter of finished solution.

11. The solution according to claim 9, wherein the acid and salt content does not exceed about 6 meq per liter of finished solution.

12. The solution according to claim 11, wherein the acid and salt content is in the range of about 2 to 4 meq per liter of finished solution.

13. The solution according to claim 9, wherein the acid and the salt are selected from one of the group consisting of citric acid, isocitric acid, 2-oxoglutaric acid, succinic acid, fumaric acid, malic acid, oxalic acid, hydrochlorides of amino acids and the salts thereof.

14. A storage system for preparing a dialysis or infusion solution, comprising:

a first container having an acid-reacting component; and a second container having an alkaline-reacting bicarbonate component, wherein the acid-reacting component is formed of at least one of a solid acid and a solid salt which is water-soluble and not hygroscopic, and which has a buffer capacity resulting in a finished solution having an acid and salt concentration of no greater than about 6 mmol per liter of solution and a bicarbonate concentration of up to about 40 mmol per liter of solution.

15. The storage system according to claim 14, wherein the acid and the salt are selected from one of the group consisting of citric acid, isocitric acid, 2-oxoglutaric acid, succinic acid, fumaric acid, malic acid, oxalic acid, hydrochlorides of amino acids and the salts thereof.

16. The storage system according to claim 14 wherein the second container is adapted for holding the alkaline-reacting bicarbonate component in the form of a solid.

17. The storage system according to claim 14, further comprising a third container holding additives.

18. The storage system according to claim 17, wherein the first, second and third containers are adapted for holding components and additives in the form of solids.

19. The storage system according to claim 17, wherein the additives include NaCl.

* * * * *